US010129672B2

(12) United States Patent
Jones (10) Patent No.: US 10,129,672 B2
(45) Date of Patent: Nov. 13, 2018

(54) HEARING DEVICE COMPRISING A SIGNAL GENERATOR FOR MASKING TINNITUS

(71) Applicant: Oticon A/S, Smørum (DK)

(72) Inventor: Gary Jones, Smørum (DK)

(73) Assignee: OTICON A/S, Smørum (DK)

( * ) Notice: Subject to any disclaimer, the term of this patent is extended or adjusted under 35 U.S.C. 154(b) by 220 days.

(21) Appl. No.: 15/176,403

(22) Filed: Jun. 8, 2016

(65) Prior Publication Data

US 2016/0366527 A1 Dec. 15, 2016

(30) Foreign Application Priority Data

Jun. 9, 2015 (EP) .................................. 15171199.1

(51) Int. Cl.
| | |
|---|---|
| *H04R 25/00* | (2006.01) |
| *A61B 5/12* | (2006.01) |
| *A61M 21/00* | (2006.01) |
| *H04R 3/04* | (2006.01) |

(52) U.S. Cl.
CPC ............. *H04R 25/75* (2013.01); *A61B 5/128* (2013.01); *A61M 21/00* (2013.01); *A61M 2021/0027* (2013.01); *H04R 25/552* (2013.01)

(58) Field of Classification Search
CPC ................ H04R 25/75; H04R 25/552; A61M 2021/0027; A61M 21/00; A61B 5/128
See application file for complete search history.

(56) References Cited

U.S. PATENT DOCUMENTS

| | | | |
|---|---|---|---|
| 5,325,872 | A | 7/1994 | Westermann |
| 6,047,074 | A | 4/2000 | Zoels et al. |
| 2005/0110700 | A1 | 5/2005 | Terry |
| 2005/0255843 | A1 | 11/2005 | Hilpisch et al. |
| 2011/0222621 | A1 | 9/2011 | Christensen et al. |
| 2015/0164381 | A1* | 6/2015 | Rush ...................... A61B 5/128 381/73.1 |

FOREIGN PATENT DOCUMENTS

| | | |
|---|---|---|
| DE | 102008025485 A1 | 7/2009 |
| EP | 1777644 A1 | 4/2007 |

(Continued)

*Primary Examiner* — Christine H Matthews
*Assistant Examiner* — Joshua D Lannu
(74) *Attorney, Agent, or Firm* — Birch, Stewart, Kolasch & Birch, LLP (57) ABSTRACT

A hearing device adapted to a specific user comprises a) a forward path for processing an electric signal representing sound, and comprising an input unit, a signal processing unit, and an output unit, b) a configurable tinnitus signal generator for generating a tinnitus masking signal intended to relieve a tinnitus of the user, and c) a combination unit operationally connected to the configurable tinnitus signal generator and to the forward path, d) an analysis path comprising d1) an analysis unit for providing a forward path analysis control signal; d2) a control unit for receiving the forward path analysis control signal, and providing a resulting tinnitus control signal based on a predefined criterion involving said number of control input signals, wherein the control unit is adapted to control the configurable tinnitus signal generator, depending on the resulting tinnitus control signal, to thereby adaptively control a level of the tinnitus masking signal.

20 Claims, 7 Drawing Sheets

(56) References Cited

FOREIGN PATENT DOCUMENTS

| EP | 2533550 A1 | 12/2012 | |
|---|---|---|---|
| WO | WO 2005/053179 A1 | 6/2005 | |
| WO | WO 2005/055654 A1 | 8/2005 | |
| WO | WO 2008/106975 A2 | 9/2008 | |
| WO | WO 2008/106975 A3 | 9/2008 | |
| WO | WO 2008106975 A2 * | 9/2008 | ............. H04R 25/75 |
| WO | WO 2012/069074 A1 | 5/2012 | |
| WO | WO 2012069074 A1 * | 5/2012 | ............. H04R 25/00 |

* cited by examiner

HEARING DEVICE COMPRISING A SIGNAL GENERATOR FOR MASKING TINNITUS

TECHNICAL FIELD

The present application relates hearing devices, e.g. hearing aids, relieving tinnitus of a user, in particular using a tinnitus masking signal. The disclosure relates specifically to a hearing device comprising a forward path for processing an electric input signal and an analysis path for analyzing a signal of the forward path with respect to a risk of noise induced tinnitus and providing a control signal to influence the processing of the electric input signal in dependence thereof.

The application furthermore relates to a binaural hearing system.

Embodiments of the disclosure may e.g. be useful in applications such as hearing aids, headsets, ear phones, active ear protection systems, and combinations thereof.

BACKGROUND

To reduce the perceived effect of tinnitus, a tinnitus sound generator is often used to mask other sounds, but thereby reducing the listener's sensitivity to sources in the environment, to speech, or to other meaningful cues. Such masking could be lessened by attenuating the tinnitus sound as other sound sources appear. A system that first determined that a sound was present and only then began attenuating the tinnitus noise would react too late to affect masking of the stimulus onset, which frequently carries important identifying information for both speech and non-speech sounds. Thus, an early start to the attenuation of the level of the tinnitus sound has key potential advantages.

U.S. Pat. No. 5,325,872A describes a tinnitus masker with one or more signal generators, a controllable amplifier, one or two electroacoustic transducers for conversion of electrical signals into acoustic signals and a voltage source, whereby at least one of the signal generators generates a continuously repeated, sinusoidal pure tone signal which slowly moves through the audio frequency range and whose cycle duration can be adjusted between 0.1 and 1000 seconds.

U.S. Pat. No. 6,047,074A describes a digital hearing aid employable for tinnitus therapy, as well as for retraining tinnitus therapy, in combination with correction of other hearing impairments of a user of the hearing aid. The hearing aid contains a signal processing chain, between a hearing aid input and a hearing aid output, which is responsible for producing a useful signal by acting on the input signal in a manner to correct the hearing impairment of a user of the hearing aid. The signal processing chain also includes an arrangement for generating a tinnitus therapy signal, which is combined in the signal processing chain with the useful signal, dependent on a mode of operation which has been selected or set.

EP2533550A1 describes a listening device for a hearing impaired person being subjected to a tinnitus at a tinnitus frequency range. The listening device comprises a controllable filter for filtering an electric input signal such that a component of the electric input signal in the tinnitus frequency range is dampened if a detection signal indicates that the electric input signal is a broadband signal or left unattenuated, if not.

SUMMARY

An object of the present application is provide an alternative solution in a hearing device or system to problems related to tinnitus.

Objects of the application are achieved by the invention described in the accompanying claims and as described in the following.

A Hearing Device

In an aspect of the present application, an object of the application is achieved by a hearing device adapted to a specific user and comprising a forward path for processing an electric signal representing sound, the forward path comprising an input unit for providing an electric input signal representing sound, a signal processing unit for processing the electric input signal and providing a processed electric signal, and an output unit for providing stimuli perceivable by a user as sound based on an electric output signal, and said signal processing unit being operatively connected to said input and output units, the hearing device further comprising a configurable tinnitus signal generator for generating a tinnitus masking signal intended to relieve a tinnitus of the user, and a combination unit operationally connected to said configurable tinnitus signal generator and to said forward path, the combination unit being configured to—at least in a specific tinnitus masking mode—provide that said electric output signal comprises said tinnitus masking signal, an analysis path comprising an analysis unit for analyzing a signal of the forward path and for providing a forward path analysis control signal;

a control unit for receiving a number of control input signals including said forward path analysis control signal, and for providing a resulting tinnitus control signal based on a predefined criterion involving said number of control input signals, wherein—at least in said specific tinnitus masking mode—said control unit is adapted to control said configurable tinnitus signal generator, depending on said resulting tinnitus control signal, to thereby adaptively control a level of said tinnitus masking signal.

Thereby an improved scheme for combining a tinnitus relief signal with a sound signal picked up from the environment is provided.

The 'tinnitus sound' is taken to be any sound that is presented by the hearing device, (e.g. a instrument) in order help the listener to cope with his/her tinnitus. In some hearing devices, 'noise' of various SPECTRAL shapes (including white, pink, red as well as other shapes that can be created by the hearing care professional (HCP) during fitting of the hearing device to a particular user) is provided, possibly with various TEMPORAL modulation patterns, e.g. ocean sounds. A benefit of the 'tinnitus sound' is believed to be that it gives the listener something else to listen to besides their tinnitus percept.

The processing program looks for increases in microphone level that might indicate the onset of a sound in the environment. This is done in very brief time windows, on the order of milliseconds, in order to be able to begin attenuating the tinnitus sound before a sound onset has completed. Level changes can be monitored in a narrow frequency band or across multiple frequency bands. When the input level increases markedly, the device begins attenuating the level of the tinnitus noise. Here a "marked increase" would be when the level in the brief time window exceeds the level in a slower level tracker by more than a pre-programmed amount. If the microphone level continues to increase, the rate of attenuation of the tinnitus noise is increased. Also, if the initial increase in microphone level is particularly high, a higher rate of attenuation of the tinnitus noise would be used.

In an embodiment, the analysis unit is configured to determine a level of said signal of the forward path (e.g. the electric input signal). In an embodiment, the control unit is configured to control the level of the tinnitus masking signal relative to a level of the signal of the forward path (e.g. the electric input signal).

In an embodiment, the control unit is configured to attenuate the tinnitus masking signal relative to the signal of the forward path when the predefined criterion is fulfilled, at least for a predefined or configurable period of time or until the predefined criterion is no longer fulfilled. In an embodiment, the control unit is configured to attenuate the tinnitus masking signal relative to the signal of the forward path when the predefined criterion is fulfilled, at least for a predefined or configurable period of time or until the predefined criterion is no longer fulfilled. In an embodiment, the analysis unit comprises a classification unit configured to classify a signal of the forward path as relevant to the user or irrelevant to the user and providing a classification signal indicative thereof (either as a binary or probabilistic value). In an embodiment, the control unit is configured to control the configurable tinnitus signal generator in dependence on the classification signal. In an embodiment, the classification unit is trained to identify signals that are particularly interesting to the user. In an embodiment, the classification unit is trained to identify signals that are un-interesting to the user.

In an embodiment, the predefined criterion relates to dynamic timing properties of the signal of the forward path. In an embodiment, the predefined criterion comprises dynamic timing properties defining trigger events in the signal of the forward path. In an embodiment, the predefined criterion is based on the signal of the forward path (e.g. the electric input signal) in the time domain (broadband signal).

In an embodiment, the predefined criterion is based on properties of the signal of the forward path in the time-frequency domain. In an embodiment, the predefined criterion is based on properties of the signal of the forward path (e.g. the electric input signal) in the time-frequency domain (band split signal).

In an embodiment, the predefined criterion relates only to one or more frequency ranges or bands of the signal of the forward path. In an embodiment, the predefined criterion relates only to one or more low-frequency ranges or bands of the signal of the forward path (e.g. the electric input signal), e.g. in the frequency range below 2 kHz.

In an embodiment, the predefined criterion relates to a rate of change of the level of the signal of the forward path. In an embodiment, the analysis unit is configured to determine the rate of change (d/dt) of the level of the signal of the forward path (e.g. the electric input signal), e.g. on a broadband level or on frequency band level. In an embodiment, the analysis unit comprises an onset detector to determine the rate of change of the level of the signal of the forward path (e.g. the electric input signal). In an embodiment, the analysis unit is configured to provide that the tinnitus masking signal is controlled in dependence of the rate of change of the level of the signal of the forward path (e.g. the electric input signal, e.g. on a frequency band level). In an embodiment, the analysis unit is configured to provide that the tinnitus masking signal is attenuated when the rate of increase of the level of the signal of the forward path is larger than a predefined threshold value. In an embodiment, the predefined criterion relates to a dynamic (e.g. time-varying) range of levels of the signal of the forward path. In an embodiment, the analysis unit comprises a level estimation unit configured to track a top level of the signal of the forward path (e.g. the electric input signal) and provide a resulting top-tracker signal. In an embodiment, the analysis unit comprises a level estimation unit configured to track a bottom level of the signal of the forward path (e.g. the electric input signal) and provide a resulting bottom-tracker signal. The provision of top- and bottom-trackers from an input audio signal is e.g. described in WO2005086536A1. In an embodiment, the analysis unit is configured to control the tinnitus masking signal in dependence of a difference between the top and bottom tracker levels. In an embodiment, the analysis unit is configured to provide that the tinnitus masking signal is attenuated when the difference between the top and bottom tracker levels is larger than a predefined threshold value. The analysis and level estimation may be conducted on the full band signal (time-domain) or on multiple band signals (frequency domain).

In an embodiment, the adaptive control of a level of said tinnitus masking signal is performed gradually. In an embodiment the attenuation of the tinnitus masking signal is performed gradually (over time) with a view to minimizing the introduction of artifacts in the resulting (combined signal) For example, a more gradual level decrease might be quite beneficial by simultaneously, 1) decreasing masking by the tinnitus sound, 2) avoiding any distracting effects you might get from a sharp level drop, and 3) providing a subtle secondary cue to the potential presence of a source in the environment. Preferably, a gradual attenuation of the tinnitus masking signal is initiated prior to the acoustic event in the signal of the forward path that fulfils the predefined criterion. Thereby an attenuation of the tinnitus masking signal can be gradually applied (to avoid or minimize the introduction of artifacts) while still allowing a user to hear the acoustic event in the signal of the forward path that fulfils the predefined criterion.

In an embodiment, the analysis unit comprises first and second level detectors for estimating first and second levels of the signal of the forward path (e.g. the electric input signal), the first and second level estimates being determined with first and second time constants, wherein the first time constant is smaller than the second time constant. The first (or relatively fast) level detector is configured to estimate a first level of the signal of the forward path with a first (relatively small) time constant, whereas the second (relatively slow) level detector is configured to estimate a second level of the signal of the forward path with a second (relatively large) time constant. In an embodiment, the relatively slow and the relatively fast level detectors provide average level estimates over a longer time window and a short time window, respectively.

In an embodiment, the control unit is configured to repeatedly determine a difference between corresponding values of the first and second level estimates and to provide said forward path analysis control signal in dependence thereof.

In an embodiment, the control unit is configured to control the level of the tinnitus masking signal in dependence of the difference between corresponding values of the first and second level estimates. In an embodiment, the control unit is configured to control the level of the tinnitus masking signal in dependence of the difference between corresponding values of the first and second level estimates. In an embodiment, the control unit is configured to attenuate the tinnitus masking signal when the difference between corresponding values of the first and second level estimates is larger than a predefined threshold value. In an embodiment, the control unit is configured to attenuate the tinnitus masking signal more the larger the difference between corresponding values of the first and second level estimates. In an embodiment, the control unit is configured to attenuate the tinnitus masking signal relative to the signal of the forward path when the predefined criterion is fulfilled for a period of time, wherein the period of time is determined in dependence of the difference between corresponding values of the first and second level estimates. In an embodiment, the control unit is configured to attenuate the tinnitus masking signal for a longer time the larger the difference between corresponding values of the first and second level estimates.

In an embodiment, the analysis path and the forward path are configured to provide that an attenuation of the tinnitus masking signal can be effectuated in time so that a sequence of the signal of the forward path fulfilling said predefined criterion can be presented to the user, while the tinnitus masking signal is attenuated (or absent). In an embodiment, the analysis unit is configured to identify steep transients (step like changes) in the signal of the forward path (e.g. in the electric input signal). Preferably such steep transients are identified early on in the forward path, e.g. after an analogue to digital (AD) converter applied to a signal from the input transducer. The control unit is preferably configured to control the tinnitus signal generator to provide that the tinnitus masking signal is attenuated before the part of the signal of the forward path comprising the steep transient in question is presented to the user. In an embodiment, the delay of the analysis path (comprising the analysis and control units) is smaller than the delay of the forward path (comprising the signal processing unit). In an embodiment, the accumulated delay of the analysis unit, the control unit and the tinnitus signal generator is smaller than the delay of the signal processing unit. In an embodiment, the combination unit is located in the forward path after the signal processing unit.

In an embodiment, the analysis unit comprises a voice activity detector for identifying a human voice in the input signal and providing an output indicative thereof, and wherein the predefined criterion comprises a condition based on an output from the voice activity detector. In an embodiment, the analysis unit comprises a voice activity detector for identifying a human voice in the signal of the forward path (e.g. the electric input signal) and providing an output indicative thereof (either on a probabilistic or binary level, and either on a broadband or a frequency band level). In an embodiment, the predefined criterion comprises a condition based on an output from the voice activity detector, its fulfilment e.g. depending on a human voice being present (with a probability larger than a predefined threshold).

In an embodiment, the analysis unit comprises an alarm detector for identifying predefined alarm signals in the input signal and providing an output indicative thereof, and wherein the predefined criterion comprises a condition based on an output from the alarm detector. In an embodiment, the analysis unit comprises an alarm detector for identifying predefined alarm signals in the signal of the forward path (e.g. the electric input signal) and providing an output indicative thereof (either on a probabilistic or binary level, and either on a broadband or a frequency band level), and wherein the predefined criterion comprises a condition based on an output from the alarm detector, its fulfilment e.g. depending on a predefined alarm signal being present. In an embodiment, the alarm detector is trained to identify relevant alarm signals in a user's environment that are or may be important for the user to hear, e.g. fire alarm, burglar alarm, etc. In an embodiment, the alarm detector is trained to identify other relevant signals in the user's environment that are or may be important for the user to hear, e.g. a dog's barking, a telephone ringing, etc.

In an embodiment, the hearing device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

Use

In an aspect, use of a hearing device as described above, in the 'detailed description of embodiments' and in the claims, is moreover provided. In an embodiment, use is provided in a system comprising one or more hearing instruments, headsets, ear phones, active ear protection systems, etc.

A Binaural Hearing System

In a further aspect, a binaural hearing system comprising a first and second hearing devices as described above, in the 'detailed description of embodiments', and in the claims, is moreover provided.

In an embodiment, the binaural hearing system is adapted to establish a communication link between the first and second hearing devices to provide that information (e.g. control and status signals, possibly audio signals) can be exchanged or forwarded from one to the other.

In an embodiment, the binaural hearing system comprises a binaural hearing aid system.

In an embodiment, the first and second hearing devices are configured to exchange information related to the onset timing of a signal of the forward path (e.g. the electric input signal) of the respective first and second hearing devices. In an embodiment, the information related to the onset timing of a signal of the forward path includes the number of control input signals to the control unit and/or the resulting tinnitus control signal from the control unit of the first and second hearing devices. In an embodiment, a comparison of the information related to the onset timing of a signal of the forward path exchanged between the first and second hearing devices is performed in each of the first and second hearing device and a result thereof is used to influence the resulting tinnitus control signal in the respective hearing devices (e.g. using a Boolean relation (e.g. AND or OR) or a weighting of the respective signals).

In an embodiment, the binaural hearing system is configured to establish a communication link between the first and/or second hearing devices and an auxiliary device. In an embodiment, the auxiliary device forms part of the binaural hearing system. In an embodiment, the auxiliary device comprises a remote control device for controlling functionality of the binaural hearing system. In an embodiment, the auxiliary device comprises a cellular telephone, e.g. a smartphone. In an embodiment, the auxiliary device, fully or partially, implements a user interface of the binaural hearing system. In an embodiment, the auxiliary device comprises a voice activity detector allowing to estimate whether or not (or with what probability) a human voice is present in an environment signal picked up by the auxiliary device. In an embodiment, the auxiliary device is configured to transmit such information to the first and or second hearing device (e.g. if a voice is present, or when a voice starts and/or ends).

Definitions

In the present context, a 'hearing device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit for processing the input audio signal and an output means for providing an audible signal to the user in dependence on the processed audio signal. In some hearing devices, an amplifier may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. SmartPhones), public-address systems, car audio systems or music players. Hearing devices, hearing systems or binaural hearing systems may e.g. be used for compensating for a hearing impaired person's loss of hearing capability, augmenting or protecting a normal-hearing person's hearing capability and/or conveying electronic audio signals to a person.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

FIG. 1 shows five embodiments (FIG. 1A, FIG. 1B, FIG. 1C, FIG. 1D and FIG. 1E) of a hearing device according to the present disclosure. FIG. 1 generally illustrates a hearing device (HD) adapted to a specific user and comprising a forward path for processing an electric signal representing sound. The hearing device is configurable in the sense that it can be operated in a number of different modes or according to a number of different hearing device programs, each mode or program being e.g. optimized to a specific task, e.g. a specific listening situation. The number of different modes or hearing device programs comprises a specific tinnitus masking mode (or program). The forward path comprises an input unit (IU) for providing an electric input signal IN representing sound, a signal processing unit (SPU) for processing the electric input signal IN and providing a processed electric signal PS, and an output unit (OU) for providing stimuli (Acoustic output) perceivable by a user as sound based on an electric output signal OUT. The output unit may comprise a loudspeaker, but may—depending on the specific application—alternatively or additionally, comprise one or more output electrodes for providing electric signals to a cochlear implant type of hearing device, or, alternatively or additionally, comprise a vibrator for providing bone conducted hearing (so the output 'Acoustic stimuli' are intended to be interpreted in this light). The signal processing unit (SPU) is operatively connected to the input (IU) and output (OU) units. The signal processing unit is preferably configured to apply a frequency and level dependent gain to the electric input signal (or a signal of the forward path derived therefrom), e.g. to compensate for a user's hearing impairment (and/or to compensate for a noisy acoustic environment). The hearing device further comprises a configurable tinnitus signal generator (TSG) for generating a tinnitus masking signal TINS intended to relieve a tinnitus of the user, and a combination unit (CU), e.g. a selection unit or a mixing unit, e.g. a SUM unit, or a weighted SUM unit, operationally connected to the configurable tinnitus signal generator (TSG) (via tinnitus masking signal TINS) and to the forward path (via processed signal PS). The combination unit (CU) is configured to—at least in a specific tinnitus masking mode—provide that the electric output signal OUT (provided by the combination unit based on input signals PS and TINS) comprises said tinnitus masking signal TINS. The hearing device (HD) further comprises an analysis path comprising an analysis unit (ANA) for analyzing a signal IN of the forward path and for providing a forward path analysis control signal, and a control unit (CNT) for receiving a number of control input signals including said forward path analysis control signal, and for providing a resulting tinnitus control signal ($CTR_1$) an possibly one or more additional control signals for controlling other functional units of the hearing device based on a predefined criterion involving the number of control input signals (e.g. $CTR_1$, $CTR_2$, $CTR_3$). The control unit (CNT) is adapted to control the configurable tinnitus signal generator (TSG), depending on the resulting tinnitus control signal ($CTR_1$), to thereby adaptively control a level of the tinnitus masking signal TINS (at least in the specific tinnitus masking mode). The additional control signals may e.g. comprise a control signal $CTR_2$ for controlling the combination unit (CU), e.g. adapted to control the selection or mixing of the input signals to the combination unit. The additional control signals may e.g. comprise (dashed line) control signal $CTR_3$ for controlling the signal processing unit (SPU), e.g. to enter or leave a specific mode of operation of the hearing device, e.g. the specific tinnitus masking mode.

The tinnitus signal generator (TSG) is configurable in the sense that the level of the generated tinnitus masking signal can be controlled via the tinnitus control signal ($CTR_1$). In further embodiments, the tinnitus control signal is also configurable in frequency content, and/or modulation. In an embodiment, the tinnitus masking signal can be selected among a number of different kinds of signals (either stored in the hearing device or generated by an algorithm stored in the hearing device (or a combination thereof)), e.g. among a number of different natural sounds, e.g. ocean waves, artificially generated sounds, etc. Such selection of the tinnitus control signal can e.g. be provided via a user interface (cf. unit UI in FIG. 1C, 1D, 1E, FIG. 3, and FIG. 5).

Figure 1A:
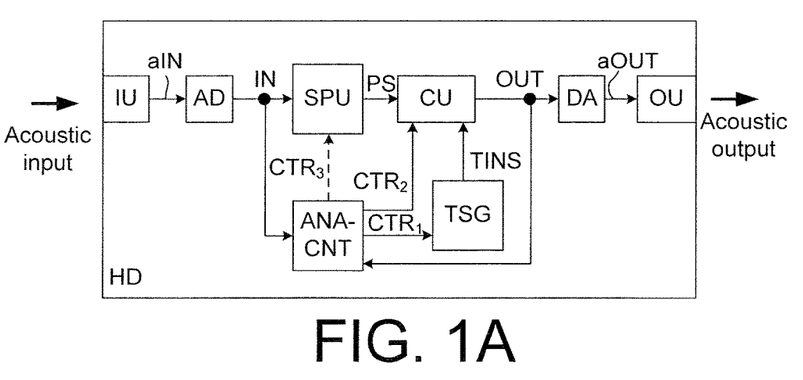
FIG. 1 shows five embodiments (FIG. 1A, FIG. 1B, FIG. 1C, FIG. 1D and FIG. 1E) of a hearing device according to the present disclosure.

FIG. 1A shows a first embodiment of a hearing device as described above. The only difference is that the forward path of the embodiment of FIG. 1A (in addition to the input unit (IU), the signal processing unit (SPU), the combination unit (CU), and the output unit (OU)) comprises analogue to digital (AD) and digital to analogue (DA) converters. The AD converter is inserted between the input unit (IU) and the signal processing unit (SPU) to digitize an analogue input signal aIN from the input unit (IU) and providing a digitized electric input signal IN. Likewise, the DA converter is inserted between the combination unit (CU) and output unit (OU) to convert digitized electric output signal OUT into an analogue output signal aOUT fed to the output unit (OU).

Figure 1B:
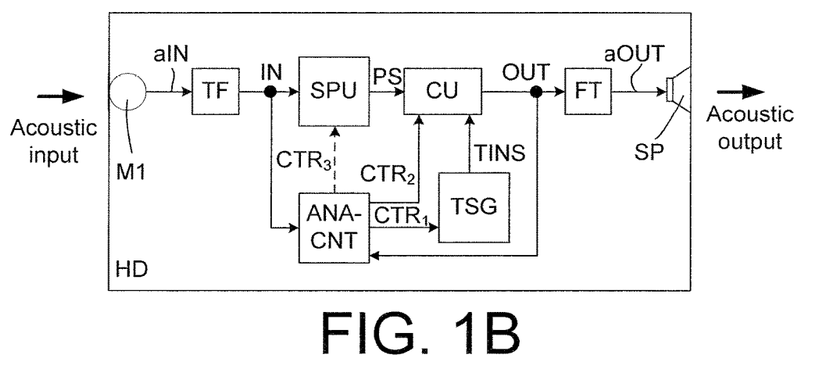
Figure 1C:
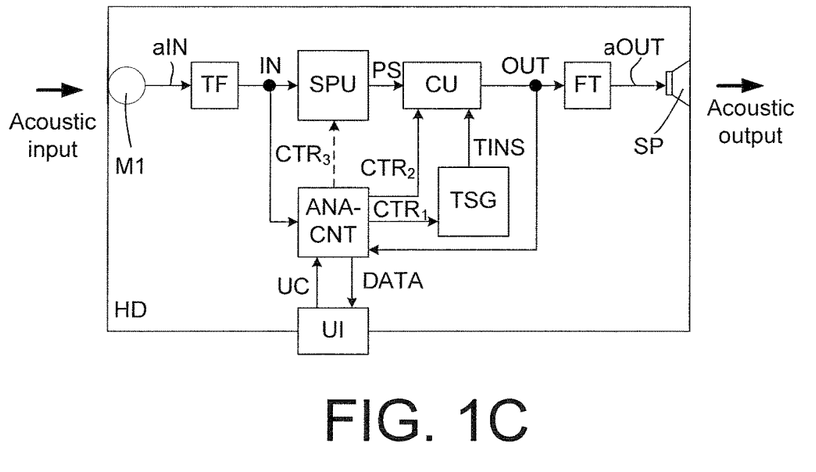
Figure 1D:
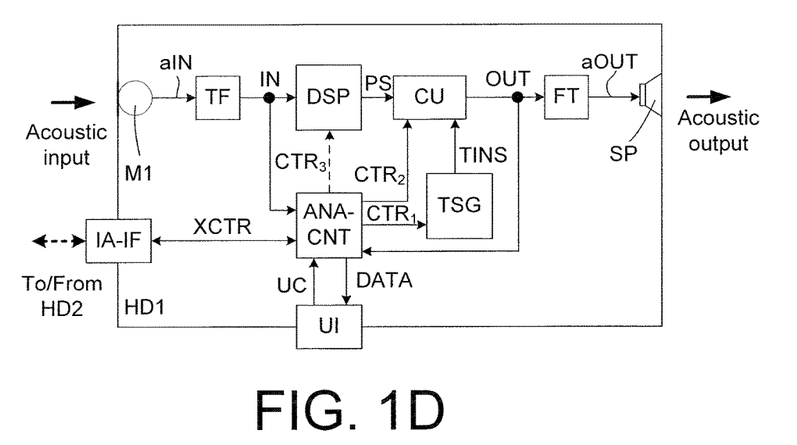

In general, the embodiments of FIG. 1 may be freely configured (according to the particular application) to provide that some or all signal processing of the analysis path and/or the forward path is conducted in the frequency domain (e.g. as specifically indicated in FIG. 1B, 1C, 1D). Alternatively, in other embodiments, some or all signal processing of the analysis path and/or the forward path is conducted in the time domain. It is to be understood that even if no time to frequency domain converters (and inversely) are indicated in a particular drawing, such converters may be present (e.g. assumed to form part of other functional parts).

FIG. 1B shows a second embodiment of a hearing device according to the present disclosure. The embodiment of FIG. 1B is identical to the embodiment of FIG. 1A apart from the following differences. The input unit (IU in FIG. 1A) is implemented as a microphone (M1) for converting an environment sound (Acoustic input) to an analogue electric input aIN. The output unit (OU in FIG. 1A) is implemented as a loudspeaker (SP) for converting an analogue electric output aOUT to a sound (Acoustic output) to be presented to a user. In the forward path of the embodiment of FIG. 1B the isolated AD and DA converters are substituted by time domain to frequency domain (TF) and frequency domain to time domain (FT) converters, respectively (assumed to include the respective AD and DA functionality, as needed). Thereby the signal processing of the forward path can be performed in a number of frequency bands. Likewise, the signal processing of the analysis path can be performed in a number of frequency bands. In an embodiment, the number of frequency bands used for processing in the forward and analysis paths is identical, but may alternatively be different. In an embodiment, the number of frequency bands used for processing in the analysis path is smaller than in the forward path. In an embodiment, processing in the analysis path is performed in the time domain (to reduce delays induced by time to frequency domain conversion). This may e.g. be implemented in the embodiment of FIG. 1B by branching the signal to the analysis path (to the analysis and control unit ANA-CNT) off prior to time to frequency domain conversion unit (TF, e.g. an analysis filter bank) (but preferably after an AD-conversion) and by moving the combination unit CU to after the frequency to time domain conversion unit (FT, e.g. a synthesis filter bank) (but preferably before a DA-conversion). Alternatively, the identification of the acoustic event fulfilling the predefined criterion may be implemented in the analogue regime to reduce delay of the relevant part of the analysis path (e.g. by branching off the signal aIN of the forward path before it is digitized, and implementing relevant parts of the analysis path in the analogue domain).

FIG. 1C shows a third embodiment of a hearing device according to the present disclosure. The embodiment of FIG. 1C is identical to the embodiment of FIG. 1B apart from the following differences. The embodiment of FIG. 1C further comprises a user interface (UI) allowing a user to influence the functionality of the hearing device (cf. control signal UC), e.g. to initiate a particular mode of operation of the hearing device (including the specific tinnitus masking mode), to select a type of tinnitus masking signal, etc. Further, the user interface may be used to display data (cf. signal DATA) of relevance to the present function of the hearing device. In an embodiment, the user interface (UI) is implemented in a separate auxiliary device, e.g. a remote control device (e.g. implemented in a smartphone or the like), so that the hearing device comprises appropriate antenna and transceiver circuitry to allow communication with the auxiliary device.

FIG. 1D shows a fourth embodiment of a hearing device (HD1) according to the present disclosure. The embodiment of FIG. 1D is identical to the embodiment of FIG. 1C apart from the following differences. The embodiment of FIG. 1D further comprises an inter-aural communication interface (IA-IF) to a contra-lateral hearing device of a binaural hearing system allowing an exchange of information between first and second hearing devices of a binaural hearing system (cf. e.g. FIG. 3). The inter-aural communication interface (IA-IF) comprises appropriate antenna and transceiver circuitry to allow communication between the first and second hearing devices (HD1, HD2). In an embodiment, the first and second hearing devices are configured to exchange information related to the onset timing of a signal of the forward path (e.g. the electric input signal) of the respective first and second hearing devices, cf. signal XCTR received from (and transmitted to) the second hearing device (HD2) (as indicated by To/From HD2 in FIG. 1D).

Figure 1E:
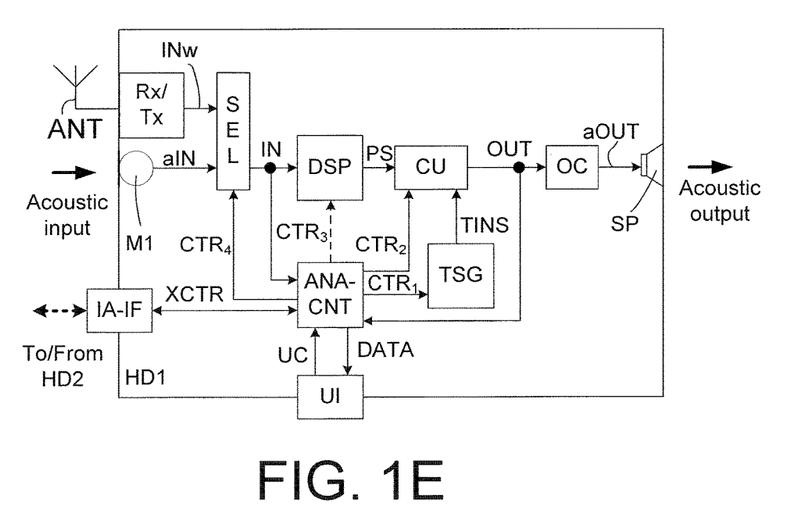

FIG. 1E shows a fifth embodiment of a hearing device (HD1) according to the present disclosure. The embodiment of FIG. 1E is identical to the embodiment of FIG. 1D apart from the following differences. The embodiment of FIG. 1E further comprises a communication interface to an auxiliary device, e.g. a sound delivery device, e.g. from a TV-set or other entertainment device (e.g. a music player), a telephone (AD, see e.g. FIG. 5), etc. The hearing device (HD1) comprises appropriate antenna and transceiver circuitry (ANT, Rx/Tx) to allow communication with the auxiliary device, at least including reception of a wireless signal (e.g. an audio signal, an information signal or a combination thereof, cf. input signal INw. The hearing device (HD1) further comprises an input converter and selection unit IC-SEL operationally connected to the microphone unit (M1) and to the antenna and transceiver circuitry (ANT, Rx/Tx) allowing a selection of one of the two input signals aIN and INw at a given time. The selection unit (IC-SEL) may comprise AD- and TF-converters as appropriate (or the output INw of the transceiver (Rx/Tx) may be in digitized form) and substitutes the TF-converter of FIG. 1D. The selection unit (SEL) is controlled via control signal $CTR_1$ from the control unit (CNT) (i.e. the control part of combined analysis and control unit (ANA-CNT) of FIG. 1E), e.g. via the user interface. The forward path comprises an output converter (OC, instead of FT-converter of FIG. 1D) to provide digital to analogue and/or frequency to time domain conversion as appropriate.

FIG. 2 shows four embodiments (FIG. 2A, FIG. 2B, FIG. 2C, and FIG. 2D) of an analysis and control unit according the present disclosure. The analysis and control unit (ANA CNT) generally comprises an analysis unit (ANA) and a control unit (CNT) operationally connected to each other via a number (≥1) of control input signals FPAC (forward path analysis control signals) from the analysis unit (ANA). The analysis unit (ANA) receives a number p of input signals $FW_1, FW_2, \ldots, FW_p$ branched off from the forward path, where p is larger than or equal to 1. The analysis and control unit (ANA-CNT) may further comprise a number of detectors (or receive a number of input signals from separate detectors in communication with the hearing device) providing further information about the acoustic environment of the hearing device (e.g. forming part of a classification unit (CLU), cf. FIG. 2B, 2D). The control unit (CNT) provides a number q of (output) control signals $CTR_1, CTR_2, \ldots, CTR_q$, where q is larger than or equal to 1 based on a number of control input signals. At least one of the (output) control signals (termed 'the resulting tinnitus control signal'), (e.g. $CTR_1$ as in FIG. 1, 3, 4) is configured to control the configurable tinnitus signal generator (TNG in FIG. 1, 3, 4), in particular to adaptively control a level of said tinnitus masking signal in dependence of the number of control input signals (including the forward path analysis control signal(s) FPAC).

Figure 2A:
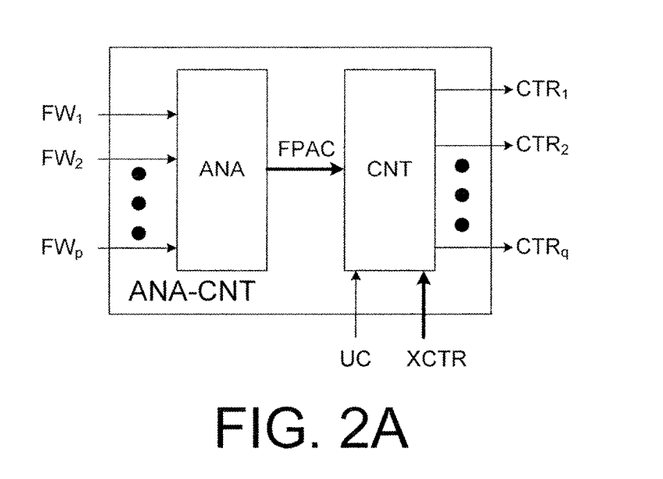
FIG. 2 shows four embodiments (FIG. 2A, FIG. 2B, FIG. 2C, and FIG. 2D) of an analysis and control unit according the present disclosure.

FIG. 2A shows a first embodiment of an analysis and control unit (ANA-CNT) as described above. The only difference is that the control unit (CNT) additionally receives control input signals UC and XCTR. The input control signal UC is a control signal from a user interface (UI, cf. FIG. 1D, 1E, 3, 5). Control signal UC may e.g. contain control information regarding the mode of operation (e.g. corresponding to a particular listening program, e.g. a tinnitus mode) of the hearing device, a control of the (default) ratio of mixture of the tinnitus masking signal with a signal of the forward path, a selection of a type of tinnitus masking signal, etc. (see e.g. FIG. 5).

Figure 2B:
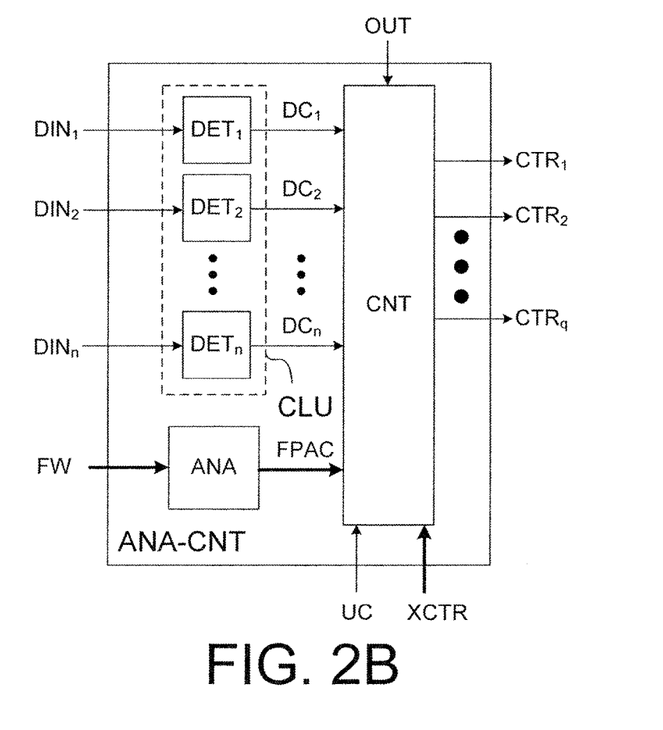

FIG. 2B shows a second embodiment of an analysis and control unit (ANA-CNT) as described above and in connection with FIG. 2A. The embodiment of FIG. 2B additionally comprises a number of detectors $DET_1, DET_2, \ldots, DET_n$, each providing a detector control signal $DC_1, DC_2, \ldots, DC_n$, each being indicative of a property of the physical (e.g. the acoustic) environment, or of the user (e.g. a mental state or cognitive load). The detector control signals $DC_1, DC_2, \ldots, DC_n$ are fed to the control unit (CNT) and used in the generation of the output control signals $CTR_1, CTR_2, \ldots, CTR_q$, for controlling the tinnitus signal generator (TSG) and other units (e.g. the signal processing unit (SPU), the combination unit (CU), the selection/mixing unit (SEL, SEL-MIX) of the hearing device 11D. The detectors each receive a detector input signal $DIN_1, DIN_2, \ldots, DIN_n$, representing a property of the environment or the user, e.g. a signal from a separate microphone located in the environment (or attached to a particular speaker), a physical property of the environment or the user (e.g. a temperature), a current brainwave signal of the user, etc. As in FIG. 2A, the analysis unit (ANA) receives input signal(s) (indicated by bold arrow denoted FW) and provides forward path analysis control signal(s) (indicated by bold arrow denoted FPAC). In the embodiment of FIG. 2B, the detectors are indicated to form part of a classification unit (CLU). The classification unit is in general configured to classify the environment around (e.g. the acoustic environment) and/or the state of the user. The classification unit is e.g. configured to classify a signal of the forward path as relevant to the user or irrelevant to the user and providing a classification signal indicative thereof (either as a binary or probabilistic value). In the embodiment of FIG. 2B, the control unit further receives the electric output signal OUT to consider together with other control input signals. The output signal OUT may be used (e.g. in comparison with the signal of the forward path (e.g. input signal IN)) to verify whether an identified acoustic event (intended to be heard by the user) in the input signal can be identified in the output signal OUT when presented to the user.

Figure 2C:
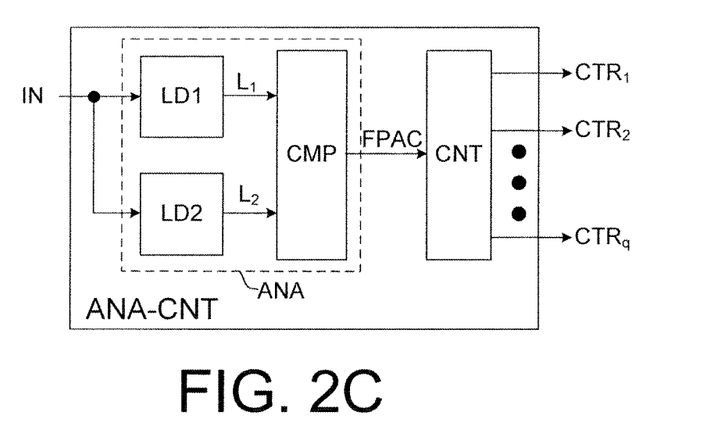

FIG. 2C shows a third embodiment of an analysis and control unit (ANA-CNT) as described above and in connection with FIG. 2A. The analysis unit (ANA) of FIG. 2C comprises first and second level detectors (LD1 and LD2) for estimating first and second levels ($L_1, L_2$) of the signal of the forward path (e.g. the electric input signal IN). The first (or relatively fast) level detector (LD1) is configured to estimate a first level ($L_1$, represented by signal $L_1$) of the signal of the forward path with a first (relatively small) time constant, whereas the second (relatively slow) level detector (LD2) is configured to estimate a second level ($L_2$, represented by signal $L_2$) of the signal of the forward path with a second (relatively large) time constant. The analysis unit (ANA) further comprises a comparison unit (CMP) configured to (repeatedly) compare the first and second level estimates ($L_1, L_2$,) and to decide whether the difference between the two levels is sufficiently large to indicate an onset of an acoustic event that the user should attend to (and thus result in an attenuation (e.g. disabling) of the tinnitus masking signal). In other words, the comparison unit is adapted to provide a forward path analysis control signal FPAC which is fed to the control unit (CNT) for evaluation together with possible other control input signals to provide (output) control signals $CTR_1, CTR_2, \ldots, CTR_q$, at least for controlling an output level of the tinnitus masking signal TINS (cf. e.g. FIG. 1, 3, 4). In other words, the control unit is configured to control the level of the tinnitus masking signal TINS in dependence of the difference between corresponding (simultaneous) values of the first and second level estimates $L_1, L_2$. In the embodiment of FIG. 2C, no other control input signals to the control unit (CNT) than the forward path analysis control signal FPAC are indicated. Preferably, the adaptive control of a level of the tinnitus masking signal is performed gradually (fading over time) with a view to minimizing the introduction of artifacts in the resulting (combined) signal. A gradual level decrease is advantageous by simultaneously, 1) decreasing masking by the tinnitus sound, 2) avoiding any distracting effects from a sharp level drop, and 3) providing a subtle secondary cue to the potential presence of a source in the environment. Together, the first and second level detectors (LD1 and LD2) and the comparison unit (CMP) may constitute an onset detector (OND, cf. FIG. 2D). An example of providing simultaneous level estimates using relatively fast and relatively slow level detectors is e.g. discussed in WO2003081947A1.

Figure 2D:
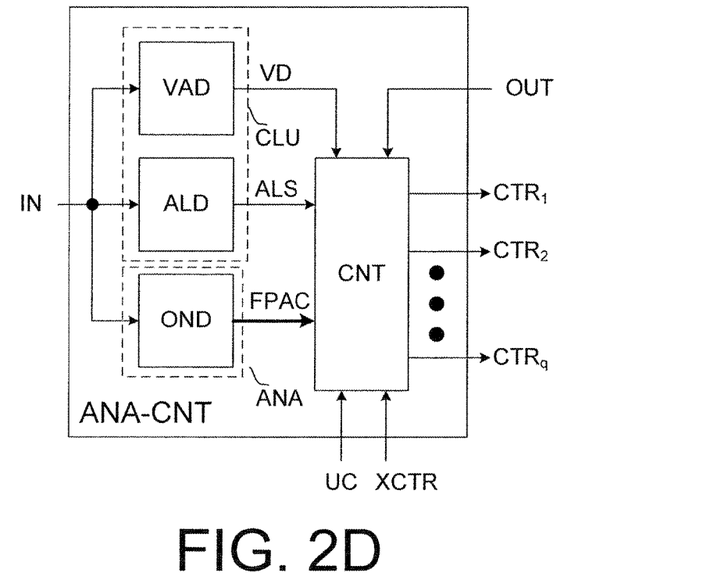

FIG. 2D shows a fourth embodiment of an analysis and control unit (ANA-CNT) as described above and in connection with FIG. 2C. The embodiment of FIG. 2D additionally comprises two detectors VAD (e.g. $DET_1$ in FIG. 2B) and ALD (e.g. $DET_2$ in FIG. 2B), each providing a detector control signal VD and ALS, respectively, each detector signal being indicative of a property of the acoustic environment (the presence or not of a voice activity and an alarm signal, respectively). The two detectors form part of a classification unit (CLU) for classifying the acoustic environment of the hearing device (and its user). The analysis unit comprises onset detector OND providing the forward path analysis control signal FPAC, as discussed in connection with FIG. 2C. The voice activity detector (VAD) is adapted for identifying a human voice in the signal of the forward path (e.g. the input signal IN) and providing an output (VD) indicative thereof (either on a probabilistic or binary level, and either on a broadband or a frequency band level). Preferably, the predefined criterion for providing a resulting tinnitus control signal based on the number of control input signals comprises a condition based on the output VD from the voice activity detector (VAD) (its fulfilment e.g. depending on a human voice being present (with a probability larger than a predefined threshold)). The alarm detector (ALD) is adapted for identifying predefined alarm signals in the signal of the forward path (e.g. in the input signal IN) and providing an output signal ALS indicative thereof (either on a probabilistic or binary level, and either on a broadband or a frequency band level). Preferably, the predefined criterion for providing a resulting tinnitus control signal based on the number of control input signals comprises a condition based on an output ALS from the alarm detector (ALD) (its fulfilment e.g. depending on a predefined alarm signal being present).

Figure 3:
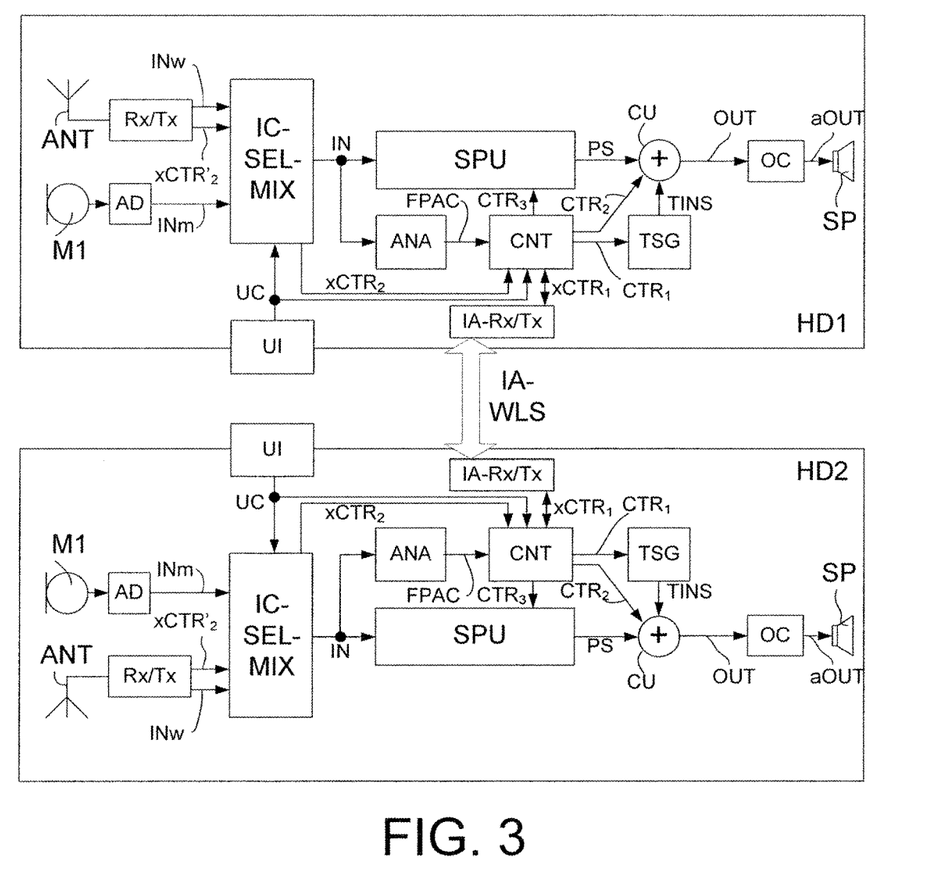
FIG. 3 shows an embodiment of a binaural hearing system according to the present disclosure.

FIG. 3 shows an embodiment of a binaural hearing system according to the present disclosure. The binaural hearing system comprises first and second hearing devices (HD1, HD2) according to the present disclosure as e.g. described in connection with FIG. 1. The embodiments of first and second hearing devices of FIG. 3 are shown to be identical (this needs not necessarily be the case though). The first and second hearing devices (HD1, HD2) of FIG. 3 are identical to the embodiment of FIG. 1E apart from the following differences. The combination unit (CU in FIG. 1) in the forward path is embodied in a SUM-unit ('+') for adding the tinnitus masking signal TINS from the tinnitus signal generator (TSG) to the processed signal PS of the forward path from the signal processing unit (SPU) and thereby providing a resulting output signal OUT. Further, the audio signal received from an auxiliary device (e.g. an audio delivery device, e.g. a wireless microphone or a cellular telephone, cf. e.g. FIG. 5) comprises an embedded information signal or a detector signal xCTR'$_2$, which is extracted in the antenna and transceiver circuitry (ANT, Rx/Tx) and forwarded to the control unit (CNT) as signal xCTR$_2$ via the IC-SEL-MIX-unit. The IC-SEL-MIX-unit allows a (possibly user controlled, cf. signal UC from the user interface (UI)) mixing of the sound signal INm picked up by the microphone (M1) with the sound signal INw received from an auxiliary device.

The first and second hearing devices (HD1, HD2) are configured to exchange information related to the onset timing of a signal of the forward path (e.g. the electric input signal) of the respective first and second hearing devices (HD1, HD2) via a wireless link (IA-WLS), e.g. an inductive link. In an embodiment, the information related to the onset timing of a signal of the forward path includes the number of control input signals to the control unit and/or the resulting tinnitus control signal from the control unit of the first and second hearing devices. In an embodiment, a comparison of the information related to the onset timing of a signal of the forward path exchanged between the first and second hearing devices is performed in each of the first and second hearing devices and a result thereof is used to influence the resulting tinnitus control signal in the respective hearing devices (e.g. using a Boolean relation (e.g. AND or OR) or a weighting of the respective signals).

Figure 4:
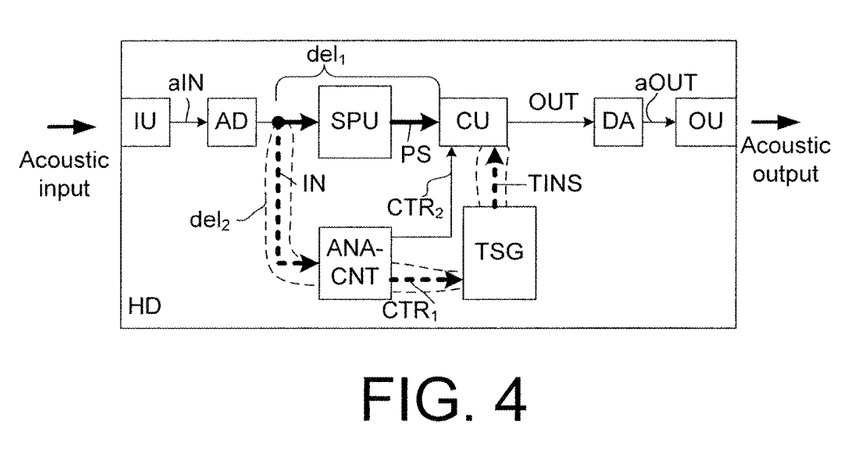
FIG. 4 shows an embodiment of a hearing device according to the present disclosure, where relevant delays of the forward path and analysis paths are indicated.

FIG. 4 shows an embodiment of a hearing device according to the present disclosure, where relevant delays of the forward path and analysis paths are indicated. Preferably, acoustic events in the signal (here IN) of the forward path that fulfills the predefined criterion (e.g. steep transients) are identified by the analysis unit (ANA) early on in the forward path, e.g. (as here) after an analogue to digital (AD) converter applied to the analogue signal aIN from the input transducer (IU). The control unit (CNT) is preferably configured to control the tinnitus signal generator (TSG) to provide that the tinnitus masking signal TINS is attenuated before the part of the signal PS of the forward path comprising the acoustic event (e.g. a steep transient) in question is presented to the user (specifically before it is combined with the tinnitus masking signal TINS in the combination unit (CU)). Preferably, the delay (del$_2$) of the analysis path (comprising the analysis and control unit (ANA-CNT) and the tinnitus signal generator (TSG), cf. dashed enclosure denoted del$_2$ in FIG. 4) is smaller than the delay (del$_1$) of the corresponding part of the forward path (between the branching off point of the signal of the forward path connected to the analysis unit (ANA-CNT) and the combination unit (CU)), here comprising the signal processing unit (SPU).

Figure 5:
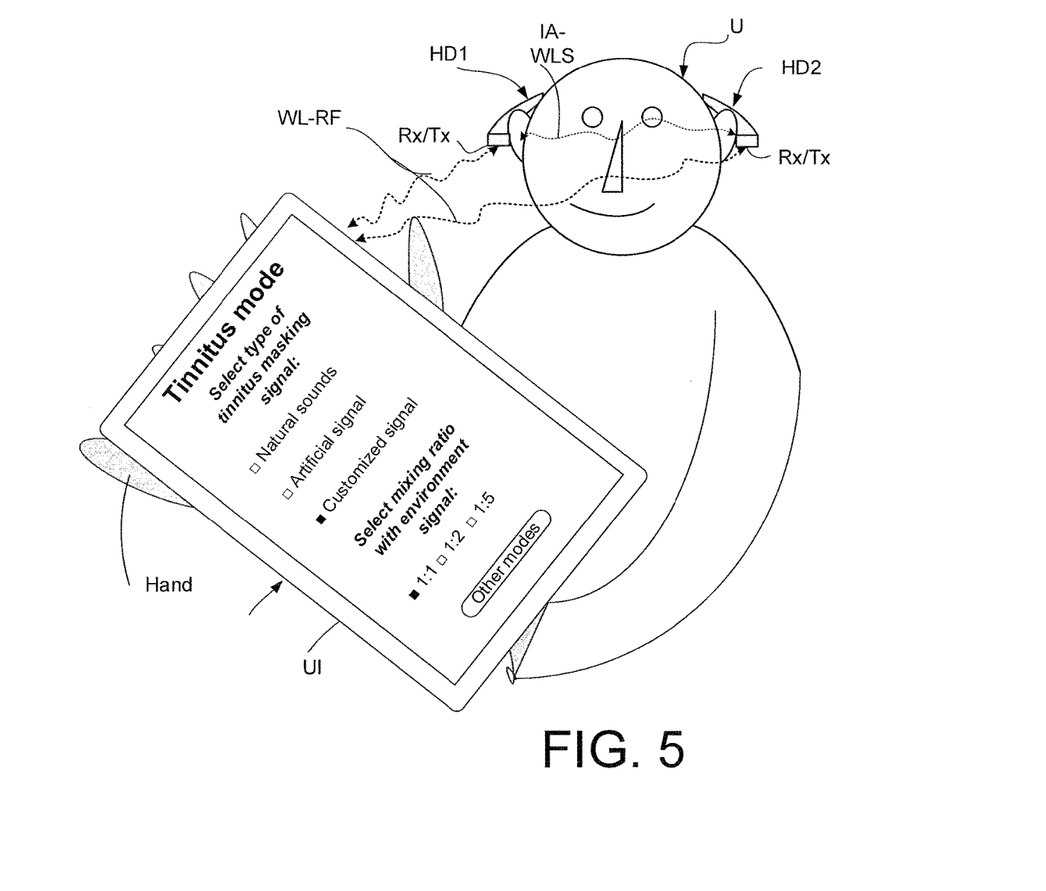
FIG. 5 shows an embodiment of a binaural hearing system comprising first and second hearing devices and an auxiliary device in communication with the hearing devices, the auxiliary device comprising a user interface for influencing a mode of operation of the binaural hearing system.

FIG. 5 shows an embodiment of a binaural hearing system comprising first and second hearing devices and an auxiliary device in communication with the hearing devices, the auxiliary device comprising a user interface for influencing a mode of operation of the binaural hearing system. Preferably, the user interface (UI) comprises a graphical interface, e.g. a (possibly touch sensitive) display. In an embodiment, a single user interface for the binaural hearing system, e.g. embodied in a separate (preferably handheld, cf. Hand in FIG. 5) auxiliary device (AD), e.g. a remote control, e.g. implemented as an APP of a communication device, e.g. a smartphone, is provided. An embodiment of such a system is illustrated in FIG. 5.

FIG. 5 shows an embodiment of a binaural hearing system comprising first e.g. (right) and second hearing (e.g. left) devices (HD1, HD2) and an auxiliary device (AD) in communication with the hearing devices. The auxiliary device (AD) comprises a user interface (UI) for influencing a mode of operation of the binaural hearing system, e.g. each of the left and right hearing devices (HD1, HD2), in particular the specific tinnitus mode of operation of the hearing devices.

The first and second hearing devices (HD1, HD2) are e.g. implemented as described in connection with FIG. 1-4. In the embodiment of FIG. 5, the binaural hearing system comprises an auxiliary device (AD) in the form of or comprising a cellphone, e.g. a smartphone. The left and right hearing assistance devices (HD1, HD2) and the auxiliary device (AD) each comprise relevant antenna and transceiver circuitry (Rx/Tx) for establishing wireless communication links between the hearing assistance devices (link IA-WLS) as well as between at least one of or each of the hearing assistance devices and the auxiliary device (link WL-RF). In an embodiment, the interaural link IA-WLS is based on near-field communication (e.g. on inductive coupling), but may alternatively be based on radiated fields (e.g. according to the Bluetooth standard, and/or be based on audio transmission utilizing the Bluetooth Low Energy standard). In an embodiment, the link WL-RF between the auxiliary device and the hearing assistance devices is based on radiated fields (e.g. according to the Bluetooth standard, and/or based on audio transmission utilizing the Bluetooth Low Energy standard), but may alternatively be based on near-field communication (e.g. on inductive coupling). The bandwidth of the links (IA-WLS, WL-RF) is preferably adapted to allow sound source signals (or at least parts thereof, e.g. selected frequency bands and/or time segments) and/or information signals, e.g. control input signals to be transferred between the devices.

As illustrated in FIG. 5 by a screen of the 'Tinnitus mode'-APP, the user (U) has the option of selecting a type of tinnitus masking signal provided by the respective tinnitus signal generators (TSG) of the hearing devices. In the example shown, the user can select between 'Natural sounds' (e.g. representing breaking waves), an 'Artificial signal' (e.g. a signal generated by a mathematical algorithm) o a 'Customized signal' (e.g. specifically adapted in frequency to the tinnitus sound(s) experienced by the use). In the example of FIG. 5, the latter has been selected, as indicated by the filled (black) square in front of option 'Customized signal'. The exemplary screen of the 'Tinnitus mode'-APP shown in FIG. 5 further allows the user to select a mixing ratio between the tinnitus masking signal and a signal of the forward path (as picked up o received by the input unit (IU) of a given hearing device. The user can choose between a number of predefined mixing ratios (1:1, 1:2, and 1:5). In the example of FIG. 5, the first ratio has been selected, as indicated by the filled (black) square in front of option '1:1'. Further, the exemplary screen of the 'Tinnitus mode'-APP gives the user the option of having other modes of operation presented (cf. activation field 'Other modes' at the bottom of the screen). Other user options regarding the tinnitus mode of operation (as well as other modes) may be implemented as appropriate.

Various aspects of inductive communication links (IA-WLS) are e.g. discussed in EP1777644A1, US20050110700A1, and US2011222621A1. WO2005055654A1 and WO2005/053179A1 describe various aspects of a hearing aid comprising an induction coil for inductive communication with other units. A protocol for use in an inductive communication link is e.g. described in US 20050255843A1.

In an embodiment, the RF-communication link (WL-RF) is based on classic Bluetooth as specified by the Bluetooth Special Interest Group (SIG) (cf. e.g. https://www.bluetooth.org). In an embodiment, the (second) RF-communication link is based other standard or proprietary protocols (e.g. a modified version of Bluetooth, e.g. Bluetooth Low Energy modified to comprise an audio layer).

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

U.S. Pat. No. 5,325,872A (TØPHOLM & WESTERMANN) May 7, 1994
U.S. Pat. No. 6,047,074A (Zoels et al.) Apr. 4, 2000
EP2533550A1 (OTICON) Dec. 12, 2012
EP1777644A1 (OTICON) 25 Apr. 2007
US20050110700A1 (OTICON, STARKEY) 26 May 2005
US2011222621A1 (OTICON) 15 Sep. 2011
WO2005055654A1 (STARKEY, OTICON) 16 Jun. 2005
WO2005053179A1 (STARKEY, OTICON) 9 Jun. 2005
US20050255843A1 (STARKEY, OTICON) 17 Nov. 2005

The invention claimed is:

1. A hearing device adapted to a specific user and comprising:
   a forward path for processing an electric signal corresponding to sound, the forward path comprising;
      an input unit for providing an electric input signal corresponding to sound,
      a signal processing unit for processing the electric input signal and providing a processed electric signal, and
      an output unit for providing stimuli perceivable by a user as sound based on an electric output signal, and
   said signal processing unit being operatively connected to said input and output units, the hearing device further comprising:
      a configurable tinnitus signal generator for generating a tinnitus masking signal intended to relieve a tinnitus of the user, and
      a combination unit operationally connected to said configurable tinnitus signal generator and to said forward path, the combination unit being configured to, at least in a specific tinnitus masking mode, provide that said electric output signal comprises said tinnitus masking signal,
      an analysis path comprising;
         an analysis unit for analyzing a signal of the forward path and for providing a forward path analysis control signal;
         a control unit for receiving a number of control input signals including said forward path analysis control signal, and for providing a resulting tinnitus control signal based on a predefined criterion involving said number of control input signals,
      wherein, at least in said specific tinnitus masking mode, said control unit is adapted to control said configurable tinnitus signal generator, depending on said resulting tinnitus control signal, to thereby adaptively control a level of said tinnitus masking signal,
   wherein the analysis unit comprises first and second level detectors for estimating first and second levels of the signal of the forward path, the first and second level estimates being determined with first and second time constants, wherein the first time constant is smaller than the second time constant.

2. A hearing device according to claim 1 wherein said control unit is configured to attenuate the tinnitus masking signal relative to the signal of the forward path when the predefined criterion is fulfilled, at least for a predefined or configurable period of time or until the predefined criterion is no longer fulfilled.

3. A hearing device according to claim 1 wherein said predefined criterion relates to dynamic timing properties of the signal of the forward path.

4. A hearing device according to claim 1 wherein the predefined criterion is based on properties of the signal of the forward path in the time-frequency domain.

5. A hearing device according to claim 4 wherein the predefined criterion relates to one or more frequency ranges or bands of the signal of the forward path.

6. A hearing device according to claim 1 wherein the predefined criterion relates to a rate of change of a level of the signal of the forward path.

7. A hearing device according to claim 1 wherein the adaptive control of a level of said tinnitus masking signal is performed gradually.

8. A hearing device according to claim 1 wherein the control unit is configured to repeatedly determine a difference between corresponding values of the first and second level estimates and to provide said forward path analysis control signal in dependence thereof.

9. A hearing device according to claim 1 wherein the control unit is configured to control the level of the tinnitus masking signal in dependence of the difference between corresponding values of the first and second level estimates.

10. A hearing device according to claim 1 wherein the analysis path and the forward path are configured to provide an attenuation of the tinnitus masking signal that can be effectuated in time so that a sequence of the signal of the forward path fulfilling said predefined criterion can be presented to the user, while the tinnitus masking signal is attenuated or absent.

11. A hearing device according to claim 1 wherein the analysis unit comprises a voice activity detector for identifying a human voice in the input signal and providing an output indicative thereof, and wherein the predefined criterion comprises a condition based on an output from the voice activity detector.

12. A hearing device according to claim 1 wherein the analysis unit comprises an alarm detector for identifying predefined alarm signals in a user's environment in the input signal and providing an output indicative thereof, and wherein the predefined criterion comprises a condition based on an output from the alarm detector.

13. A hearing device according to claim 12 wherein the alarm detector is trained to identify relevant signals in the user's environment that are or may be important for the user to hear.

14. A hearing device according to claim 1 comprising a hearing aid, a headset, an active ear protection systems, or combinations thereof.

15. A binaural hearing system comprising first and second hearing devices according to claim 1, wherein the binaural hearing system is adapted to establish a communication link between the first and second hearing devices to provide that information can be exchanged or forwarded from one to the other.

16. A binaural hearing system according to claim 15 configured to establish a communication link between the first and/or second hearing devices and an auxiliary device.

17. A binaural hearing system according to claim 16 wherein the auxiliary device comprises a remote control device for controlling functionality of the binaural hearing system.

18. A binaural hearing system according to claim 16 wherein the auxiliary device comprises a cellular telephone.

19. A binaural hearing system according to claim 16 wherein the auxiliary device fully or partially, implements a user interface of the binaural hearing system.

20. A binaural hearing system according to claim 16 wherein the auxiliary device comprises a tinnitus mode software application that is executed for controlling features of a specific tinnitus mode of operation of the hearing devices.

* * * * *